US008992023B2

(12) United States Patent
Perez et al.

(10) Patent No.: US 8,992,023 B2
(45) Date of Patent: Mar. 31, 2015

(54) INDICES FOR MANAGEMENT OF DRY EYE SYNDROME, CORNEAL ECTASIA, KERATOPLASTY GRAFT REJECTION AND FAILURE AND FUCHS' DYSTROPHY

(71) Applicant: University of Miami, Miami, FL (US)

(72) Inventors: Victor L. Perez, Miami, FL (US); Sonia H. Yoo, Miami, FL (US); Jianhua Wang, Miami, FL (US); Mohamed Abou Shousha, Ballwin, MO (US); Rodrigo Hoffmann, Sao Paulo (BR)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 14/247,903

(22) Filed: Apr. 8, 2014

(65) Prior Publication Data

US 2014/0300862 A1      Oct. 9, 2014

Related U.S. Application Data

(60) Provisional application No. 61/809,518, filed on Apr. 8, 2013.

(51) Int. Cl.
*A61B 3/00* (2006.01)
*A61B 3/14* (2006.01)
*A61B 3/10* (2006.01)

(52) U.S. Cl.
CPC ............... *A61B 3/102* (2013.01); *A61B 3/1005* (2013.01)
USPC .......................................... 351/246; 351/206

(58) Field of Classification Search
USPC ................................................... 351/206, 246
See application file for complete search history.

(56) References Cited

PUBLICATIONS

Abou Shousha et al., "The Use of Bowman's Layer Vertical Topographic Thickness Map in the Diagnosis of Keratoconus," 2014 by the American Academy of Opthalmology, Opthalmology, Manuscript No. 2013-1327, pp. 1-6, consisting of 6-pages.

*Primary Examiner* — Jack Dinh
(74) *Attorney, Agent, or Firm* — Christopher & Weisberg, P.A.

(57) ABSTRACT

Improved indices for the diagnosis and evaluation of conditions affecting the eye. Specifically, the indices include an Enhanced Epithelial Irregularity Factor (eEIF) for the diagnosis and evaluation of conditions such as dry eye syndrome (DES), Bowman's Ectasia Index (BEI), including enhanced BEI (eBEI) and BEI-Max, and Bowman's Relative Thinning (BRT) Index for the diagnosis and evaluation of ectatic conditions such as keratoconus, pellucid marginal degeneration, post-refractive surgery ectasia, and keratoglobus, and Descemet's Membrane Thickening Index (DMT), Descemet's Rejection Index (DRI), and Descemet's Membrane Irregularity Factor (DIF) for the diagnosis and evaluation of conditions such as keratoplasty rejection and failure and Fuchs' dystrophy. These improved indices may be incorporated into optical coherence tomography systems, or any other imaging device capable of capturing high resolution images of the cornea, for more sensitive and specific diagnosis, treatment, and monitoring of certain corneal conditions, in addition to the evaluation of new treatments.

8 Claims, 14 Drawing Sheets

INDICES FOR MANAGEMENT OF DRY EYE SYNDROME, CORNEAL ECTASIA, KERATOPLASTY GRAFT REJECTION AND FAILURE AND FUCHS' DYSTROPHY

CROSS-REFERENCE TO RELATED APPLICATION

This application is related to and claims priority to U.S. Provisional Patent Application No. 61/809,518, filed Apr. 8, 2013, entitled INDICES FOR MANAGEMENT OF DRY EYE SYNDROME, CORNEAL ECTASIA, KERATOPLASTY GRAFT REJECTION AND FAILURE AND FUCHS' DYSTROPHY, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for improved diagnosis, treatment, and monitoring of certain corneal conditions, in addition to the evaluation of new treatments. Specifically, the present invention is directed to improved indices such as an Enhanced Epithelial Irregularity Factor (eEIF) for the diagnosis and evaluation of conditions such as dry eye syndrome (DES), Bowman's Ectasia Index (BEI) and Bowman's Relative Thinning (BRT) Index for the diagnosis and evaluation of ectatic conditions such as keratoconus, pellucid marginal degeneration, post-refractive surgery ectasia, and keratoglobus, and Descemet's Membrane Thickening Index (DMT), Descemet's Rejection Index (DRI), and Descemet's Membrane Irregularity Factor (DIF) for the diagnosis and evaluation of conditions such as keratoplasty rejection and failure and Fuchs' dystrophy.

BACKGROUND OF THE INVENTION

There are many conditions that affect the eye. Some common conditions, for example, include aqueous deficiency and evaporative dry eye syndrome (DES), corneal ectasia, keratoplasty graft rejection episode and failure, and Fuchs' dystrophy. However, conditions such as these are difficult to diagnose and treat.

Dry Eye Syndrome

Dry eye syndrome (DES) is a worldwide public health problem. An estimated 25 million patients suffer from DES in the United States alone. DES adversely affects the quality of life of patients, as the condition affects vision and commonly causes constant symptoms of eye irritation, foreign body sensation, and dryness. In severe cases, DES can even compromise the integrity of the eye globe and can lead to corneal melting and blindness. Similarly, evaporative dry eye, caused by meibomian gland dysfunction (MGD), is becoming a common cause of dry eye and its diagnosis and treatment has become a challenge. Major research is directed at finding new remedies for DES but those efforts are limited by the fact that there is no gold standard for the diagnosis of DES. Available diagnostic tests lack standardization and usually are not representative of patient symptoms, in addition to other limitations.

Studies have shown poor association between current dry eye test and patient symptoms. Moreover, those tests are affected by factors that are difficult to control, making them poorly standardized tests. For example, tear breakup time is affected by temperature and humidity of the examination room. Reflex lacrimation as the patient keeps his or her eyes open to obtain measurements can invalidate the test results. The Schirmer test (in which paper strips are inserted into the eye to measure moisture production) is invasive and unpleasant to the patient. Further, hanging filter paper from a patient's eyes could result in reflex tearing that can affect obtained measurements. Fluorescein or other vital stains of the ocular surface are examples of tests that detect the injurious effect of dry eye on the ocular surface epithelium; however, results of those tests are detected using a slit lamp with magnification of only up to 16×. Such accuracy might be enough to diagnose moderate to severe dry eye, but certainly would not be enough to detect mild cases or monitor response to treatment. Indeed, the discrepancy between signs and symptoms of dry eye patients most likely stems from that insufficient accuracy. Corneal nerves are sensitive enough to detect those microscopic injuries to the ocular surface, but the available tests are not sensitive enough to visualize that injury. Another limitation of current clinical techniques is that many are subjectively evaluated. What an examiner would consider mild corneal and conjunctival fluorescein staining, another could consider moderate.

New diagnostic modalities have been recently introduced such as confocal microscopy and tear film osmolarity. Diagnosis of DES using confocal microscopy is a time-consuming procedure that requires contact with the ocular surface and that limits its use to research and makes it difficult to incorporate into everyday clinics. Furthermore, it can only capture images over a small area of the total cornea. Tear film osmolarity has shown promise as a quantitative method to diagnose DES, but it is also invasive and time consuming. Until enough data proves otherwise, lubricating a dry eye would be able to improve the health of the ocular surface by providing an alternative to the inadequate natural tears, but does not alter the tear film osmolarity. Thus, looking at the osmolarity might not provide an insight about the response of the patient to treatment.

Corneal Ectasia

Corneal ectasia is a progressive disease that adversely affects the structural integrity of the cornea. The weakened cornea bulges, and crippling irregular astigmatism starts to develop. The astigmatism degrades vision and as the disease progresses, scarring of the cornea occurs. Corneal ectasia includes keratoconus, pellucid marginal degeneration, post-refractive surgery ectasia, and other rare diseases such as keratoglobus. New modalities for the treatment of corneal ectasia have been developed, such as corneal collagen cross-linkage that uses UV light and Riboflavin to stiffen the cornea and halt the progression of the disease. It is desirable to halt the progression of the disease at a very early stage, before vision is degraded by irregular astigmatism or scarring. Post-refractive surgery ectasia is a devastating complication of refractive surgery, an elective procedure received by approximately 16 million patients in the United States in 2011. The most common cause of this complication that threatens vision in those patients is performing the refractive surgery on an early ectasia patient who was not detected by the conventional current diagnostic techniques. This highlights the need for a specific and sensitive sign that can be used to detect those early patients to save them from such a devastating complication.

Corneal topography and thickness are among the current diagnostic criteria of ectasia. Their use is complicated by their variations among the general populations. Normal range of corneal thicknesses is wide, and overlapping between normal thin corneas and early ectasia patients complicates the use of this criterion in the diagnosis of early cases of ectasia. Thus, lack of specificity is a significant limitation of using corneal thickening for the diagnosis of the ectasia. Corneal topography use in diagnosis of ectasia shares the same limitations as corneal thinning Irregular astigmatism is seen in normal subjects and in ectasia patients complicating its use to make the diagnosis, especially in mild cases.

Keratoplasty Graft Rejection/Failure and Fuchs' Dystrophy

Keratoplasty, or corneal transplantation, is used to replace a damaged or diseased cornea with a donated corneal tissue graft. About 60,000 corneal transplants are performed every year in the United States alone, it is not uncommon for a graft recipient's body to reject the donated corneal tissue. In fact, it is estimated that 50% of those patients will experience at least one episode of rejection, and 20% of transplants will ultimately fail by the third year, commonly due to the patient's immune system attacking the graft endothelium and destroying it. To preserve the graft and prolong its survival, rejection must be detected and reversed as early as possible. Unfortunately, however, the early stages of rejection are not easily identified. Currently, methods such as slit-lamp examination are used to detect rejection, but this method offers only limited magnification and mild subclinical rejection episodes are often missed. Further, performing endothelial cell count using specular microscopy lacks sufficient reproducibility, sensitivity, and specificity. Finally, measuring the central cornea thickness lack sufficient sensitivity to render it useful in the diagnosis of mild cases, and the wide range of normal corneal thickness complicates it use for diagnosis of mild corneal edema.

Fuchs' dystrophy (or Fuchs' endothelial dystrophy) is a degenerative disease of the corneal endothelium with accumulation of guttae (focal outgrowths) and thickening of Descemet's membrane. These changes can lead to corneal edema and vision loss. Although the disease is most common in people in their 50s and 60s, Fuchs' dystrophy can begin to affect people while in their 30s and 40s, so it is important to accurately identify the condition in its early stages. The same commonly used methods of detecting corneal graft rejection are often used to diagnose Fuchs' dystrophy, but these methods have the same limitations as discussed above. Additionally, there is no cut-off value that can define rejection, failure, or Fuchs' dystrophy. Similarly, using endothelial cell count is equally imprecise, as there is no cut-off value for endothelial cell count. The number of endothelial cells that can maintain a clear cornea is unknown. Further, it has been shown that reliable endothelial cell count is not possible in at least one third of Fuchs' dystrophy patients.

Fuchs' dystrophy is the leading cause of corneal transplantation in the United States, accounting for almost a quarter of all keratoplasties. About 5% of the United States population older than 40 years has Fuchs' dystrophy. This condition is an aging disease and as our population ages, the prevalence of Fuchs' dystrophy is expected to rise even more and is thus expected to impose an even more significant public health problem. Fuchs' dystrophy imposes challenge on eye banking. The confusion between normal subjects and early Fuchs' dystrophy carries the risk of either transplanting patients with early Fuchs' dystrophy corneal grafts or, on the other hand, the unnecessary wasting of corneal tissue. Further, the demand on corneal tissue is growing. The aging of the population, the increased prevalence of Fuchs' dystrophy, and the lowered threshold for endothelial keratoplasty are widening the gap between the demand and the supply. However, developing de novo corneal guttae in corneal grafts has been reported, which is most likely an effect of transplanting undiagnosed Fuchs' dystrophy grafts.

Optical coherence tomography (OCT) is a noninvasive optical signal acquisition and processing method that captures micrometer-resolution, three-dimensional images from within, for example, biological tissue. OCT has proven to be an indispensible tool for imaging the retina and the optic nerve. It has changed the practice of ophthalmology and has become the gold standard for diagnosis and management of diseases with significant morbidity and prevalence such as age-related macular degeneration and glaucoma. Nevertheless, OCT has not yet achieved such a role in anterior segment in general and cornea imaging in particular. This is most likely due to the lack of standardized clinical applications for the device in imaging the anterior segment and cornea.

It is therefore desirable to provide improved indices for diagnosing corneal conditions such as dry eye syndrome, corneal ectasia, keratoplasty rejection and failure, and Fuchs' dystrophy. It is further desirable that these improved indices be usable with current and future imaging devices such as OCT systems, or any other imaging device or system capable of providing high-resolution images of the eye and in particular the cornea, for identifying and monitoring corneal conditions.

SUMMARY OF THE INVENTION

The present invention advantageously provides a method and system for improved diagnosis, treatment, and monitoring of certain corneal conditions, in addition to the evaluation of new treatments. Specifically, the present invention is directed to improved indices such as an Enhanced Epithelial Irregularity Factor (eEIF) for the diagnosis and evaluation of conditions such as dry eye syndrome (DES), Bowman's Ectasia Index (BEI) and Bowman's Relative Thinning (BRT) Index for the diagnosis and evaluation of ectatic conditions such as keratoconus, pellucid marginal degeneration, post-refractive surgery ectasia, and keratoglobus, and Descemet's Membrane Thickening Index (DMT), Descemet's rejection index (DRI), and Descemet's Membrane Irregularity Factor (DIF) for the diagnosis and evaluation of conditions such as keratoplasty rejection and failure and Fuchs' dystrophy.

In one embodiment, a method of evaluating dry eye syndrome in a patient may comprise obtaining optical coherence images of the patient's cornea (including the epithelium) using an optical coherence system, the images being taken in at least four frames that divide the cornea into at least eight segments, calculating an enhanced epithelial irregularity factor (eEIF) value for each of the at least eight segments, the eEIF value being the mean of the standard deviation of epithelial thickness measured along each of the at least four frames, and calculating an average eEIF value, the average eEIF value being the average of the at least eight eEIF values. The average eEIF value may then be compared to a predetermined eEIF value. The at least four frames may include four frames that are at approximately 45 degrees, approximately 90 degrees, approximately 135 degrees, and approximately 180 degrees. Dry eye syndrome may be considered to be present when the average eEIF value is higher than the predetermined eEIF value. The method may further comprise evaluating the efficacy of a treatment for dry eye syndrome based at least in part on the comparison between the average eEIF value to a predetermined eEIF value, wherein the treatment is considered to be effective when the average eEIF value and the predetermined eEIF value are within a predetermined range of each other.

In another embodiment, a method of evaluating keratoconus in a patient may comprise obtaining images of the patient's cornea (including the Bowman's layer) using an optical coherence tomography system, and calculating at least one of: a measured Bowman's ectasia index (BEI) value, the BEI value being defined as a thinnest point on the Bowman's layer of the patient's cornea as measured on the optical coherence images; a measured Bowman's relative thinning (BRT) index value, the measured BRT index value being the difference between the thinnest point on the Bowman's layer superiorly and the thinnest point on the Bowman's layer inferiorly as measured on the optical coherence images; a measured enhanced Bowman's ectasia index (eBEI) value, the eBEI value being defined as a minimum Bowman's layer thickness of an inferior one-half of the cornea divided by an average thickness of the Bowman's layer of a superior one-half of the cornea multiplied by 100, the minimum Bowman's layer thickness and the average Bowman's layer thickness being as measured on the optical coherence images; and a measured enhanced maximum Bowman's ectasia index (eBEI-Max) value, the eBEI-Max value being defined as a minimum Bowman's layer thickness of the inferior one-half of the cornea divided by a maximum thickness of the Bowman's layer of the superior one-half of the cornea multiplied by 100, the minimum Bowman's layer thickness and the maximum Bowman's layer thickness being as measured on the optical coherence images. The method may further include comparing the measured BEI value to a predetermined BEI value, comparing the measured BRT index value to a predetermined BRT value, comparing the measured eBEI index value to a predetermined eBEI value, and/or comparing the measured eBEI-Max index value to a predetermined eBEI-Max value, with the comparison indicating the presence and/or severity of keratoconus. Then, the measured BEI value may be compared to a predetermined BEI value and/or the measured BRT index value may be compared to a predetermined BRT index value. The optical coherence images of the patient's cornea may include at least three images, and may be obtained using an optical coherence system delivering incident light to the patient's cornea, wherein at least one first image is obtained when the incident light is directed perpendicular to a first corresponding corneal periphery when the patient is looking in a first direction (such as when the patient is looking downward), at least one second image is obtained when the incident light is directed perpendicular to a second corresponding corneal periphery when the patient is looking in a second direction (such as when the patient is looking straight ahead), and at least one third image is obtained when the incident light is directed perpendicular to a third corresponding corneal periphery when the patient is looking in a third direction (such as when the patient is looking upward). Compilation of the at least three images by a computer processor may generate a composite corneal image of approximately 9 mm in diameter. Keratoconus may be considered to be present when the measured BEI value is less than the predetermined BEI value, when the measured eBEI value is less than the predetermined eBEI value, and/or when the measured eBEI-Max value is less than the predetermined eBEI-Max value.

In another embodiment, a method of evaluating at least one of keratoplasty rejection, keratoplasty failure, and Fuchs' dystrophy may comprise obtaining optical coherence images of the patient's cornea (including the Descemet's membrane), and calculating at least one of a measured Descemet's membrane thickening (DMT) index value, the DMT index value being defined as the average thickness of the Descemet's membrane as measured on the optical coherence images; a measured Descemet's membrane irregularity factor (DIF) index value, the measured DIF value being defined as the standard deviation of the Descemet's membrane thickness as measured on the optical coherence images; and a measured Descemet's rejection index (DRI) value, the DRI value being defined as a thickness of the Descemet's membrane divide by a total corneal thickness multiplied by a constant, the method also comprising comparing the measured DMT index value to a predetermined DMT index value, comparing the measured DIF index value to a predetermined DIF index value, and comparing the measured DRI value to a predetermined DRI value, the comparison at least one of indicating the presence of an active keratoplasty rejection, the presence of a rejected keratoplasty, differentiating between a keratoplasty rejection secondary to immunological causes and a keratoplasty failure secondary to non-immunological causes, and indicating the presence of Fuchs' dystrophy. The constant may be 33. Then, the measured DMT index value may be compared to a predetermined DMT index value, the measured DRI value may be compared to a predetermined DRI value, and/or the measured DIF value may be compared to a predetermined DIF value. A keratoplasty graft may be considered to be rejected or failed when the measured DMT index value is greater than the predetermined DMT index value. The keratoplasty graft may be considered to be actively rejecting, rejected, or failed when the measured DRI value is greater than the predetermined DRI value. Further, the keratoplasty graft may be considered to be actively rejecting, rejected, or failed when the measured DRI value is greater than the predetermined DRI value, the DRI value being greater in rejecting keratoplasty than the DRI value in failed keratoplasty. Likewise, Fuchs' dystrophy may be considered to be present when either the measured DMT index value is greater than the predetermined DMT index value or the measured DIF value is greater than the predetermined DIF value.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Enhanced Epithelial Irregularity Factor (eEIF)

Referring generally to FIGS. 1-6, figures relating to Enhanced Epithelial Irregularity Factor (eEIF) are shown. One aspect of the present invention is based on the observation that the corneal epithelium of patients with dry eye syndrome (DES) is irregular, and that irregularity can be quantified using an epithelial irregularity factor (EIF) in a standardized and objective method that correlates to the subjective symptoms of a patient. The corneal epithelium irregularity can be reversed by treatment, and therefore this factor can be used to monitor response to treatment and can be used to test new therapies.

In order to examine the epithelium, or other parts of the eye, an imaging system such as an optical coherence tomography (OCT) system may be used, including ultrahigh-resolution OCT (UHR-OCT) systems. Additionally or alternatively, any other imaging device or system may be used that is capable of providing high-resolution images of the cornea. As a non-limiting example, the image 10 of a cornea 11 shown in the lefthand side of FIG. 1 was obtained using a UHR-OCT system, whereas the image 12 shown in the righthand side of FIG. 1 was obtained using histological analysis. The comparison shows that images obtained from the UHR-OCT are an accurate representation of cellular structures of the corneal layers and the epithelium, stromal and endothelium layers can readily be identified. The corneal epithelium, Bowman's layer, intrastromal morphology (such as the corneal lamellae), and Descemet's membrane can all be visualized in this image. As a further non-limiting example, a UHR-OCT system may be used that includes a telecentric probe mounted on a slit lamp that allows for fast (24 frames per second) in vivo scanning of swaths of up to 15 mm wide of the cornea of a patient, with a resolution of approximately 2-3 μm and a depth of approximately 3 mm into the structures of the anterior segment. Further, 2D and 3D scan patterns may be generated.

Figure 6:
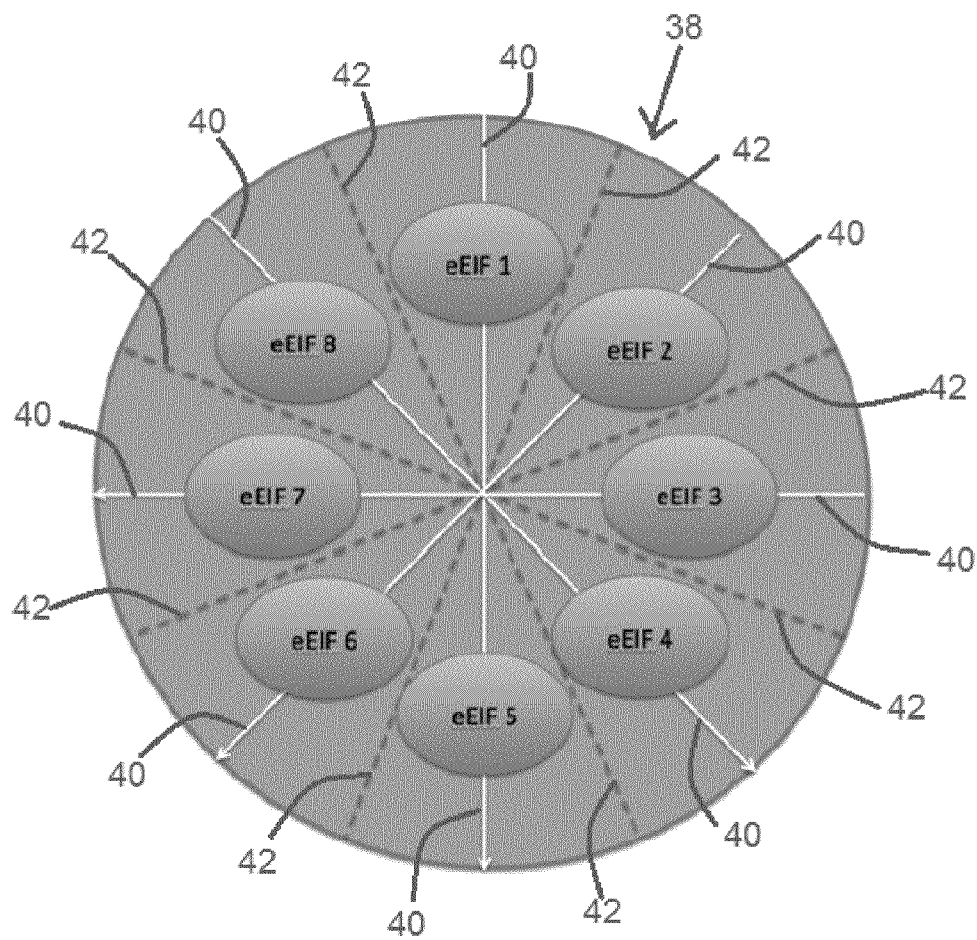
FIG. 6 shows an Enhanced Epithelial Irregularity Factor map including eight segments.

As a non-limiting embodiment of a measurement procedure, a UHR-OCT system may be used that has a resolution of 2 to 3 μm to map the corneal epithelium in a non-invasive manner to detect its irregularity. These measurements may then be used as a quantitative means to diagnose and manage DES. During the imaging session, patients may be asked to look at a central fixing target. Patients may then be asked to blink and, immediately after a blink, a radial image of their cornea may be captured using the OCT system. OCT frames may be extracted and analyzed for the purpose of describing the corneal irregularity. Then, the thickness profile of the epithelium over the central 3 mm of the cornea along extracted frames may be constructed using custom-made software. EIF and eEIF both provide non-invasive qualitative and quantitative means to diagnose DES and to develop new therapies. EIF is calculated as the standard deviation of the central 3 mm of the epithelium calculated along two (horizontal and vertical) frames. However, even though the use of EIF shows encouraging results, the fact that the factor is calculated using only two frames is a limitation that might prevent EIF from representing the cornea in its entirety. Conversely, eEIF uses four frames that "cut" the cornea at 45, 90, 135, and 180 degrees (as shown in FIG. 6). Thus, the cornea is divided into eight segments, which are used to generate an eEIF map. This eight-segment cornea map may be used to understand the distribution of corneal damage in DES. Doubling the obtained dataset (as in eEIF methods) significantly increases diagnostic precision, and thus eEIF has increased usefulness over EIF as an objective and subjective qualitative and quantitative index for the diagnosis of DES. Further, the eEIF may be used for a corneal area that extends to more than just 3 mm toward the periphery of the cornea.

Figure 1:
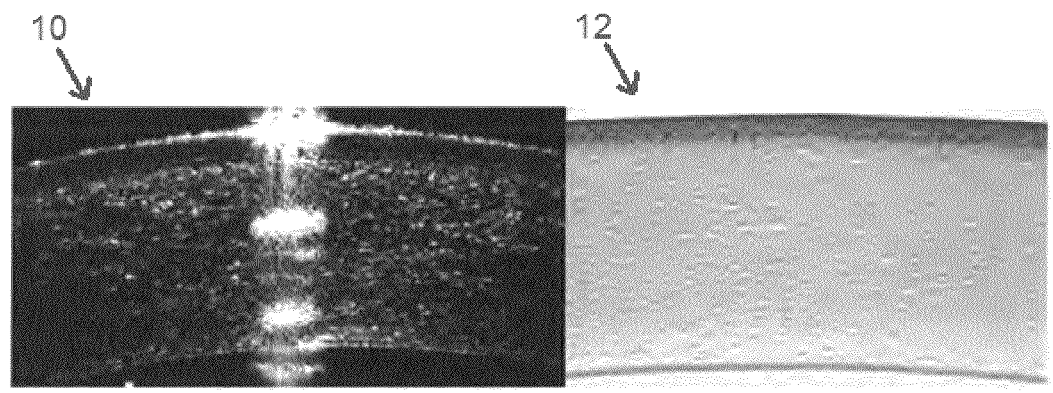
FIG. 1 shows a comparison between OCT imaging and histological analysis of the cornea, showing that OCT images are an accurate anatomic representation of the ocular surface.
Figure 2:
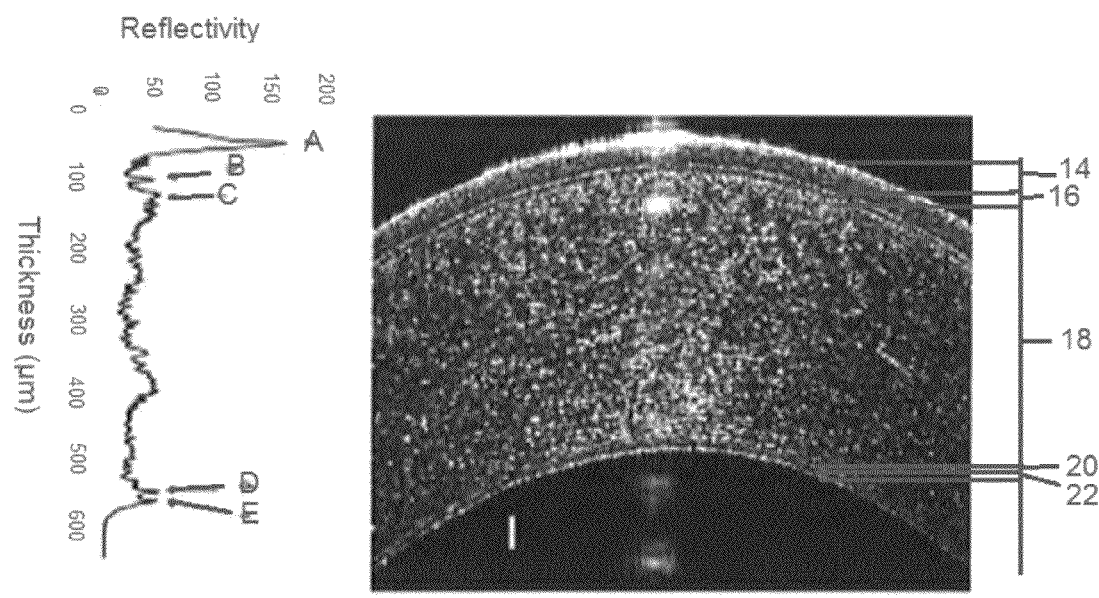
FIG. 2 shows a reflectivity profile and an OCT image, the reflectivity profile created using custom software from the OCT image.

Referring now to FIG. 2, a reflectivity profile and an OCT image are shown, the reflectivity profile created using custom software from the OCT image. These data demonstrate that OCT analysis can be used for in vivo histological pathological analysis of the ocular surface. In order to translate data from these images that can be use to quantify cellular changes in the ocular surface in patients with dry eye syndrome (DES), different measurements may be used that are based on the reflectivity profile information generated by the OCT data set. Specifically, the analysis may be focused on the quantification of the irregularities of the corneal epithelium thickness. Using a computer, the OCT image may then be converted to serials of reflectivity profiles that represent different corneal layers. This method provides a highly accurate means to measure the thickness of different corneal layers, including the epithelium 14, Bowman's layer 16, stroma 18, endothelium 20, and Descemet's membrane 22.

Continuing to refer to FIG. 2, the reflectivity profile shown on the left hand side of FIG. 2 is created using custom-made software from the OCT image shown on the right hand side of FIG. 2. Peaks are correlated to different corneal layers and used to accurately measure the thickness of different corneal layers. On the reflectivity profile, the distance from "A" to "B" represents the epithelium thickness, the distance from "B" to "C" represents the Bowman's layer thickness, the distance from "C" to "D" represents the stromal thickness, and the distance from "D" to "E" represents the Descemet's membrane thickness. The OCT images can be converted to serials of reflectivity profiles that represent different corneal layers. This method provides a highly accurate means to measure the thickness of different corneal layers.

Figure 3A:
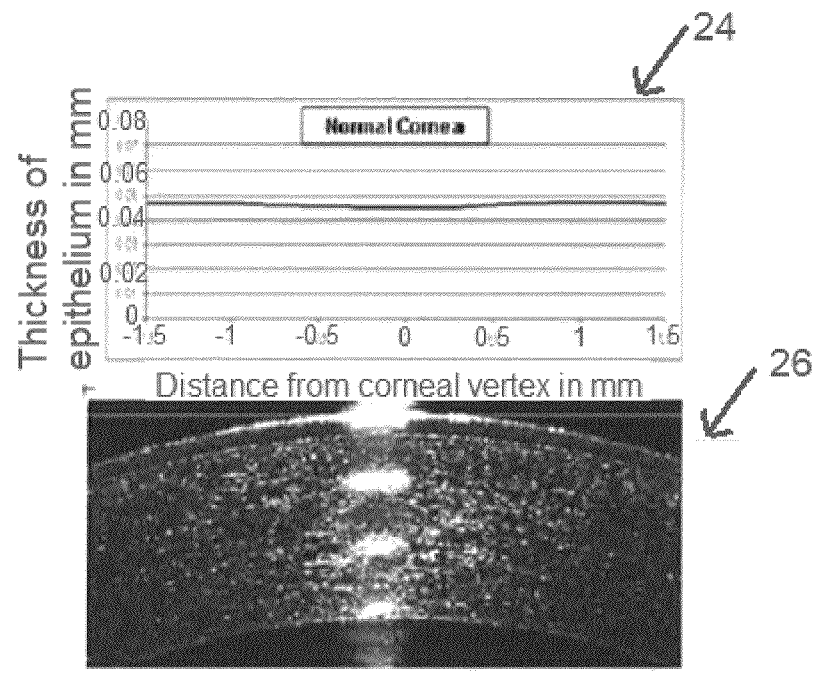
FIG. 3A shows an epithelial thickness profile and an OCT image of a normal cornea, the epithelial thickness profile generated from the OCT image.
Figure 3B:
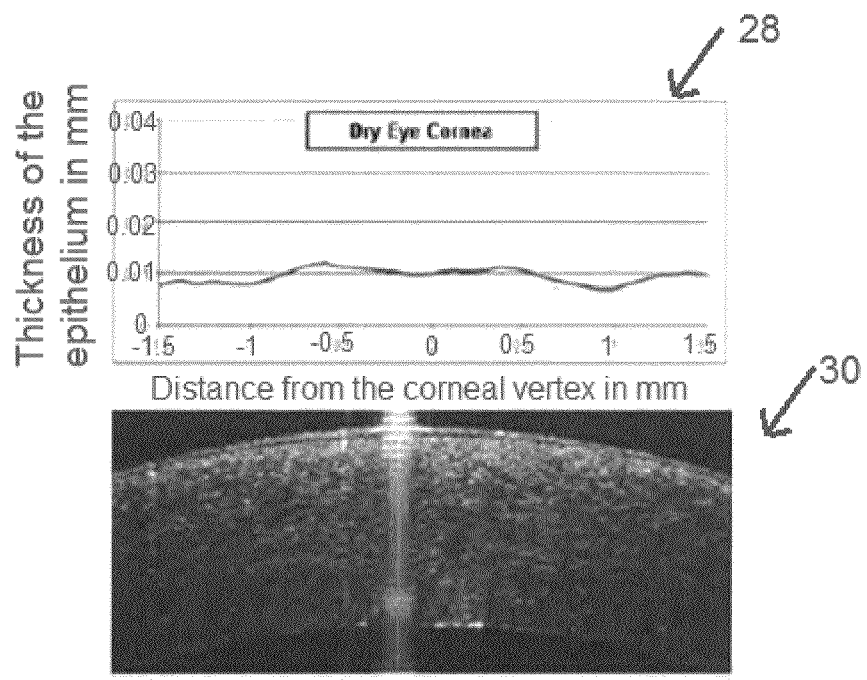
FIG. 3B shows an epithelial thickness profile and an OCT image of a dry eye cornea, the epithelial thickness profile generated from the OCT image, the epithelium being highly irregular compared to the normal cornea of FIG. 3A.
Figure 3C:
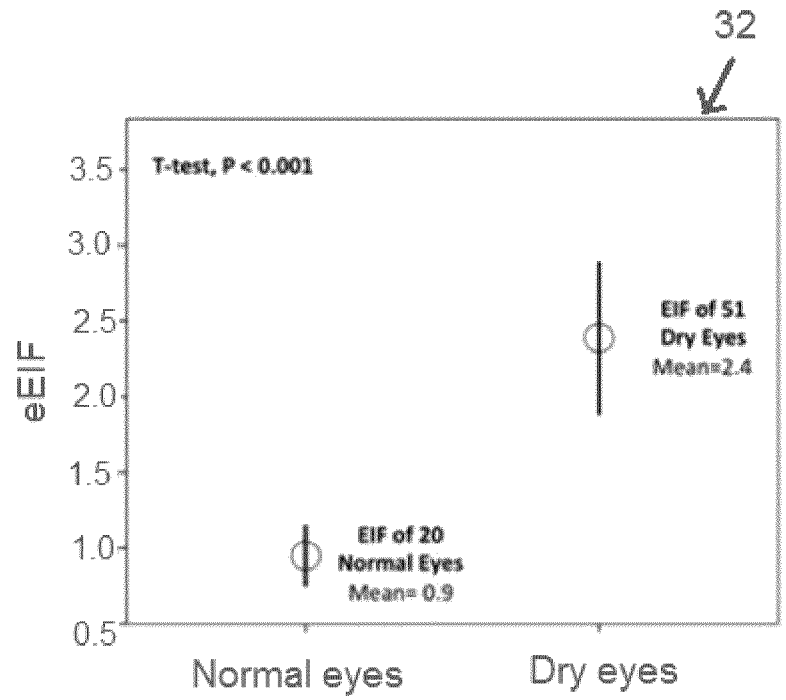
FIG. 3C shows a graph comparing Enhanced Epithelial Irregularity Factor in normal eyes and eyes with dry eye syndrome.

Referring now to FIGS. 3A and 3B, an epithelial thickness profile 24 and a corresponding OCT image 26 of a normal cornea is shown, and an epithelial thickness profile 28 and a corresponding OCT image 30 of a dry eye cornea is shown, respectively. The OCT images and reflectivity profiles shown in FIGS. 3A and 3B demonstrate that the epithelium of DES patients is irregular when compared to normal eyes (i.e. patients without DES). In order to quantify the irregularity, custom-made software was used to map the epithelial thickness along the central 3 mm of the cornea. Based on this relationship, an Enhanced Epithelial Irregularity Factor (eEIF) was developed. FIG. 3C shows a graph 32 comparing eEIF in normal eyes and in eyes with dry eye syndrome. Enhanced EIF is defined as the mean of the standard deviation of epithelial thickness measured along four frames (45, 90, 135, and 180 degrees) of the OCT image. As is shown in FIG. 3C, eEIF in DES eyes is significantly elevated when compared to normal eyes.

Figure 4:
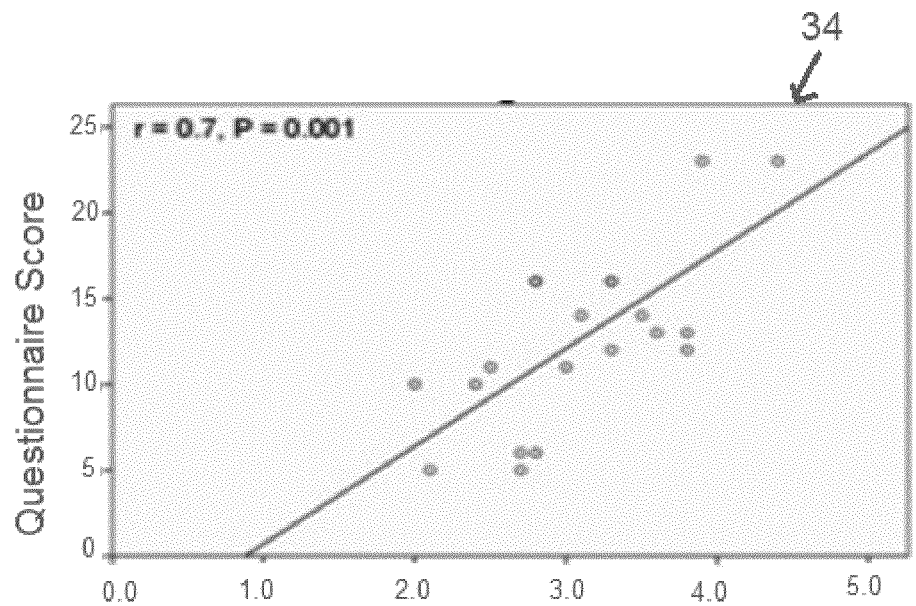
FIG. 4 shows a graph demonstrating a significant correlation between an Enhanced Epithelial Irregularity Factor of 20 dry eyes to a dry eye questionnaire score.
Figure 5:
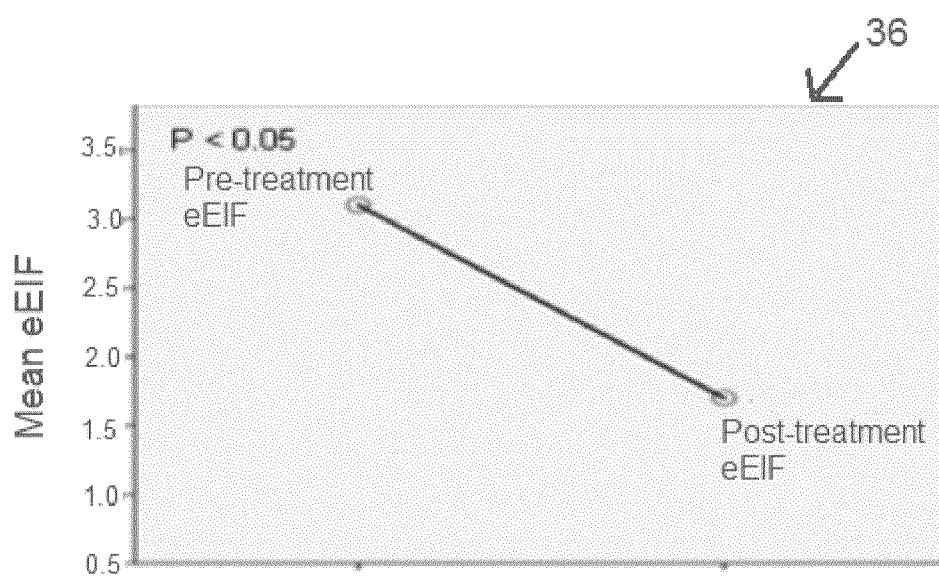
FIG. 5 shows a graph demonstrating the favorable effect of treatment using autologous serum tears on the ocular surface of eight eyes manifested by a significant decrease in Enhanced Epithelial Irregular Factor.

Referring to FIG. 4, these preliminary data suggest that eEIF could be a novel factor representative of the structural abnormalities imposed by DES on the ocular surface. Additionally, the data suggest that eEIF could be an objective means to diagnose and monitor DES. Based on these results, symptoms of DES were captured using a Dry Eye Questionnaire and correlated to eEIF. As shown in the results graph 34 of FIG. 4, eEIF correlated significantly to the questionnaire scores, which suggests that eEIF could be an objective means to describe and quantify DES and could also be an accurate indicator of the symptoms of the DES patients.

To determine whether eEIF could be used to monitor efficacy of treatment, four DES patients (eight eyes total) were prescribed autologous serum tears. The effect of this treatment was monitored over approximately 1-4 months using sequential OCT images, and the results are shown in the graph 36 of FIG. 5. As the patients experienced an improvement in their clinical signs and symptoms, it was evident that there was a significant decrease in epithelial irregularity manifested as a significant decrease in eEIF toward normal values. These data suggest that eEIF could be a novel factor to quantitatively describe the ocular surface response to treatment compounds.

Referring now to FIG. 6, an enhanced epithelial irregularity factor (eEIF) map 38 including eight segments is shown. Enhanced EIF is calculated for eight different segments of the cornea (eEIF 1, eEIF2, eEIF3, eEIF4, eEIF5, eEIF6, eEIF7, and eEIF8). Enhanced EIF is then calculated as the average of all eight segments (eEIF1 to eEIF8) and is more representative of the corneal surface than EIF. Using this map 38, eEIF may be used to understand the distribution of corneal damage in DES. In FIG. 6, arrows 40 denote the OCT scan path and dotted lines 42 represent the boundaries between the eight different regions of the cornea. The severity of DES and/or efficacy of a treatment for DES may be based at least in part on a comparison between the average eEIF value to a predetermined eEIF value (such as a predetermined value that corresponds to a normal or non-DES eye) and/or the average eEIF value before starting the treatment. DES may be considered to be present when the average eEIF value and the predetermined eEIF value are the same or within a predetermined range of each other. Similarly, a DES treatment may be considered to be effective when there is a predetermined amount of difference between the average eEIF value and the average eEIF value before starting the treatment.

Precision may be increased if the number of frames is increased from two to four. As is shown in the table below, the coefficient of variation (COV %) when two frames (90 and 180 degrees) are used decreases when four frames (45, 90, 135, and 180 degrees) are used. That is, doubling the number of frames causes eEIF to be more precise than EIF, as shown in Table 1 below:

TABLE 1

| Subjects | Type | Mean | SD | COV % | COV % with different number of frames | | | | | | |
|---|---|---|---|---|---|---|---|---|---|---|---|
| | | | | | 2 | 3 | 4 | 5 | 6 | 7 | 8 |
| 1 | Dry eye | 3.6 | 1.1 | 31.4 | 22.2 | 18.1 | 15.7 | 14.0 | 12.8 | 11.9 | 11.1 |
| 2 | Dry eye | 2.0 | 0.6 | 32.4 | 22.9 | 18.7 | 16.2 | 14.5 | 13.2 | 12.2 | 11.5 |
| 3 | Control | 1.4 | 0.2 | 15.0 | 10.6 | 8.7 | 7.5 | 6.7 | 6.1 | 5.7 | 5.3 |
| 4 | Control | 1.5 | 0.1 | 6.5 | 4.6 | 3.7 | 3.2 | 2.6 | 2.6 | 2.5 | 2.3 |
| 5 | Dry eye | 2.9 | 0.7 | 23.4 | 16.5 | 13.5 | 11.7 | 9.5 | 9.5 | 8.8 | 8.3 |
| 6 | Dry eye | 3.6 | 0.3 | 9.4 | 6.6 | 5.4 | 4.7 | 3.8 | 3.8 | 3.5 | 3.3 |

Bowman's Ectasia Index (BEI), Bowman's Relative Thinning (BRT) Index, and Enhanced Bowman's Ectasia Index (eBEI and eBEI-Max), The Bowman's layer is an acellular condensation of the anterior stroma of the cornea lying between the epithelial basement membrane and the anterior cellular stroma. It is formed of collagen fibrils that are randomly interwoven to form a dense felt-like sheet. Light and electron microscopy studies have shown that in keratoconus, the Bowman's layer undergoes disintegration that leads to irregular thinning, fragmentation, and then breaks within the layer. Those structural changes are noted when the stroma is only minimally affected, suggesting that Bowman's layer changes are possibly early pathologic changes in the disease process.

Referring generally to FIGS. 7-10B, figures relating to Bowman's Ectasia Index (BEI) and Bowman's Relative Thinning (BRT) Index are shown. In another aspect of the present invention includes highly sensitive and specific indices to diagnose ectatic diseases such as keratoconus, pellucid marginal degeneration, post-refractive surgery ectasia, keratoglobus, and the like. Those indices are referred to herein as BEI and BRT. BEI is defined as the thinnest point on the Bowman's layer calculated on 2D or 3D maps of the Bowman's layer. BRT is defined as the difference between the thinnest point on the Bowman's layer superiorly and the thinnest point inferiorly. Those highly specific and sensitive signs for the diagnosis of corneal ectasia are calculated on 2D map or 3D maps of the Bowman's layer that extends to the peripheral cornea. Using this method, unlike current techniques, it is possible to obtain 90% sensitivity and 90% specificity. Additionally, BEI is in high correlation with the severity of the disease, and therefore can be used as a qualitative as well as a quantitative diagnostic criterion for the disease.

Using OCT to create corneal epithelial maps and detecting specific changes on those maps is a new criterion for the diagnosis of ectasia and keratoconus. Additionally or alternatively, other imaging devices and/or systems may be used that are capable of providing high-resolution images of the cornea. Ectasia and keratoconus are diseases of collagen, not epithelium. Thus, this technique oversights the site of the pathology and studies a phenomenon that subsequently occurs as the result of the stromal thinning, namely, thinning of the epithelium. Thinning of the epithelium is most likely an effect of friction of the eyelid with the already bulging cornea. Additionally, the epithelium is affected by other diseases, most importantly DES, that lead to an irregular and thin epithelium. This fact denotes the lack of specificity of using the epithelium in the diagnosis of ectasia or keratoconus.

It is well known that raw OCT images are only optically correct in the central part. Beyond the central 3 mm, OCT images become warped as OCT incident light is no more perpendicular on the curved corneal surface, and thus images obtained cannot reliably represent thicknesses. Software is available to dewarp OCT images; nevertheless, dewarping OCT images decreases the quality and, in the process, sub-10 µm layers such as Bowman's layer or Descemet's membrane, as well as the fine details of the epithelium, usually become difficult to appreciate. In order to create a map of the cornea that is in focus, optically correct in all of its frames, and distinctly delineates all layers of the cornea up to the periphery of the cornea where the pathology is (in cases such as ectasia), a new imaging strategy can be used.

Figure 7A:
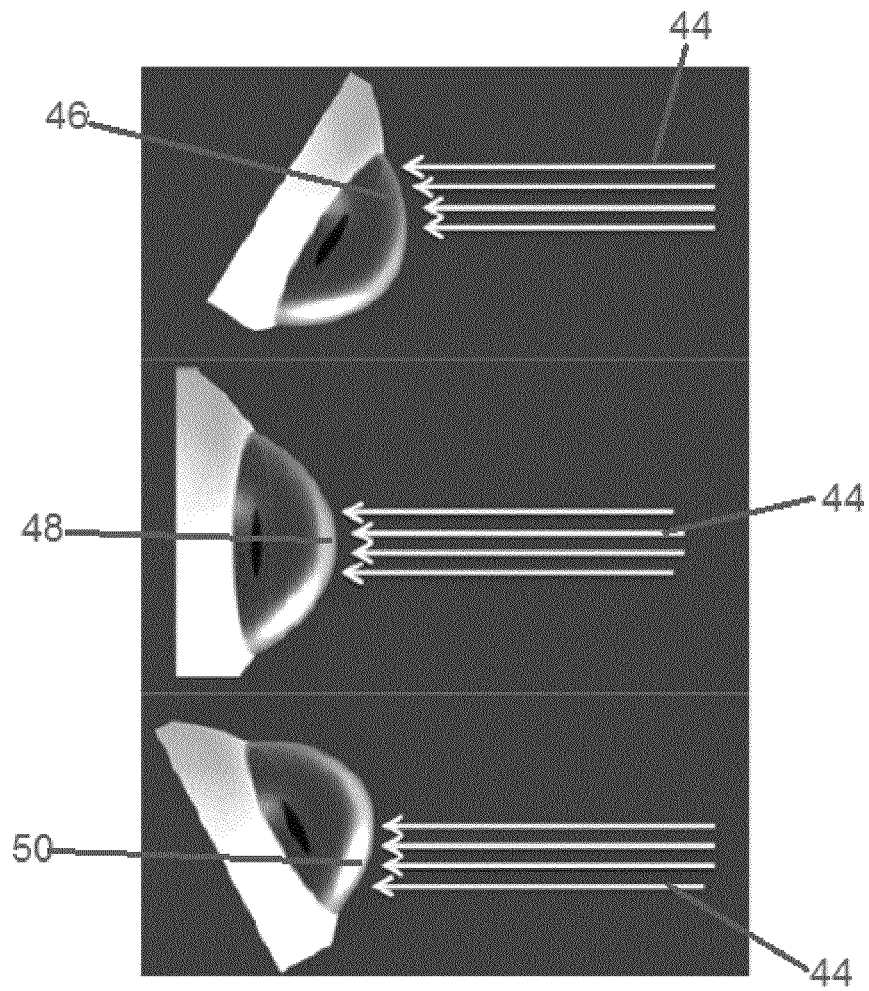
FIG. 7A shows a stylized representation of three eye positions for imaging the cornea.
Figure 7B:
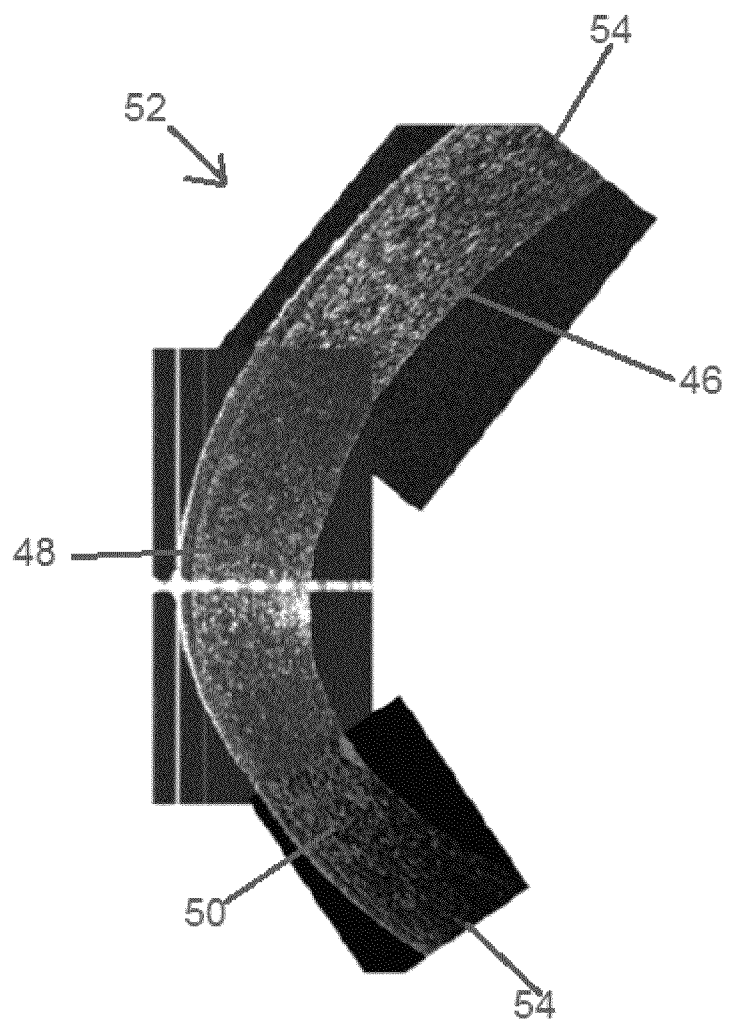
FIG. 7B shows a composite image of a cornea using three OCT-generated images, with eye positions shown in FIG. 7A.

In this novel imaging strategy, a custom-made ultra-high resolution spectral-domain anterior segment OCT (UHR OCT) system may be used. This system may have an axial resolution of about 3 µm, a center wavelength of 840 nm, bandwidth of 100 nm, a scan depth of about 3 mm, a scan width of up to 15 mm, and a scan speed of 24 frames per second. The novel imaging technique used with this system may be referred to as "limbus-to-limbus Bowman's layer topographic thickness mapping. In this technique, which overcomes the depth limitations of known OCT imaging methods, a custom-made fixation card is attached to the OCT machine. Fixation points are calibrated on the card so that as the patient looks at each, the OCT incident light 44 falls perpendicularly at the corresponding corneal periphery (for example, as shown in FIG. 7A). For example, an image of a superior one-half 46 of the cornea may be taken when the patient looks down, an image of a central one-half 48 of the cornea may be taken when the patient looks straight ahead, and an image of an inferior one-half 50 of the cornea may be taken when the patient looks up. This allows for the collection of data points sufficient to create a 9-mm vertical map of the cornea that is in focus, optically correct, and in resolution down to 3 µm along a 9-mm vertical section of the cornea (as shown in FIG. 7B). For example, the superior and inferior one-half images may be at least partially overlapped by the central one half. Compiling the data from all three frames allows for the creation of a 2D map of each corneal layer that extends to 9 mm in diameter. It will be understood that a 3D map may also be created using the same or similar method with a UHR-OCT system having extra-wide scanning capabilities. Distinction of all different layers of the cornea, namely, the epithelium, Bowman's layer, stroma, and Descemet's membrane can readily be done upon processing the captured frames. Custom-made software is used to delineate the different layers of the cornea in each captured frame and create a thickness map along that frame. This method is a novel in vivo technique that may be used to show that the Bowman's layer in patients having keratoconus undergoes relative localized inferior thinning that can be accurately quantified to differentiate with excellent sensitivity and specificity (as high as 100%) between keratoconus and normal controls.

Referring now to FIG. 7A, a graphical representation of three eye positions for imaging the cornea is shown. At least three frames that are perpendicular on the superior 46, central 48, and inferior 50 regions of the cornea can be captured, rendering three high-resolution, in-focus OCT images of the corresponding corneal region. For example, at least one image may be created of each of the superior 46, central 48, and inferior 50 regions of the cornea. With special software, a composite can be created using the three images to build a vertical map 52 of the cornea that extends to the corneal periphery 54 (as shown in FIG. 7B).

Figure 8A:
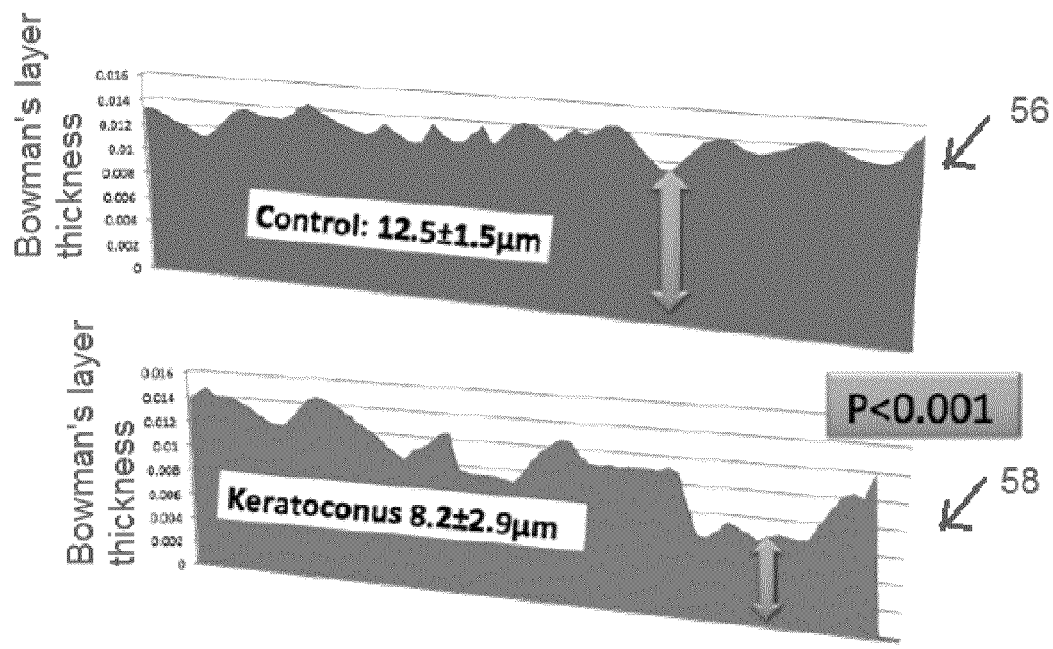
FIGS. 8A-8C show graphs comparing Bowman's layer thickness between control patients and keratoconus patients.
Figure 8B:
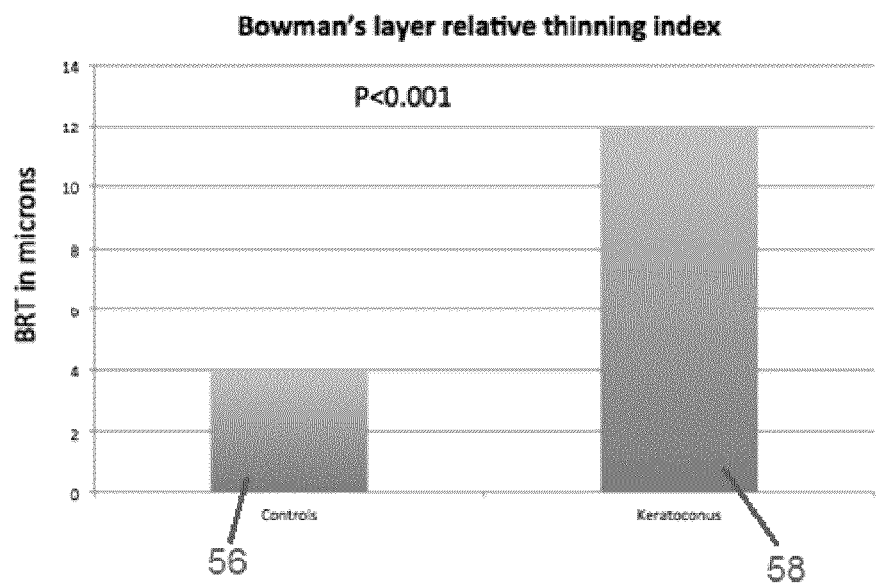
Figure 8C:
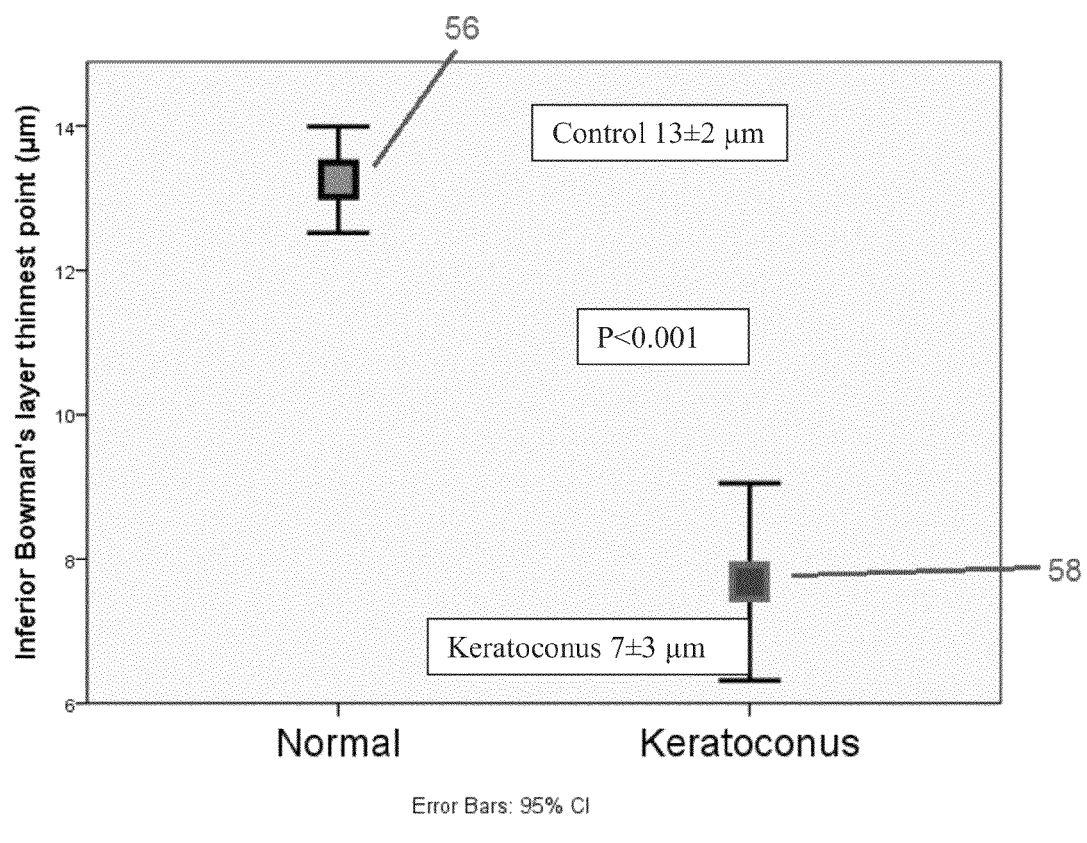
Figure 8D:
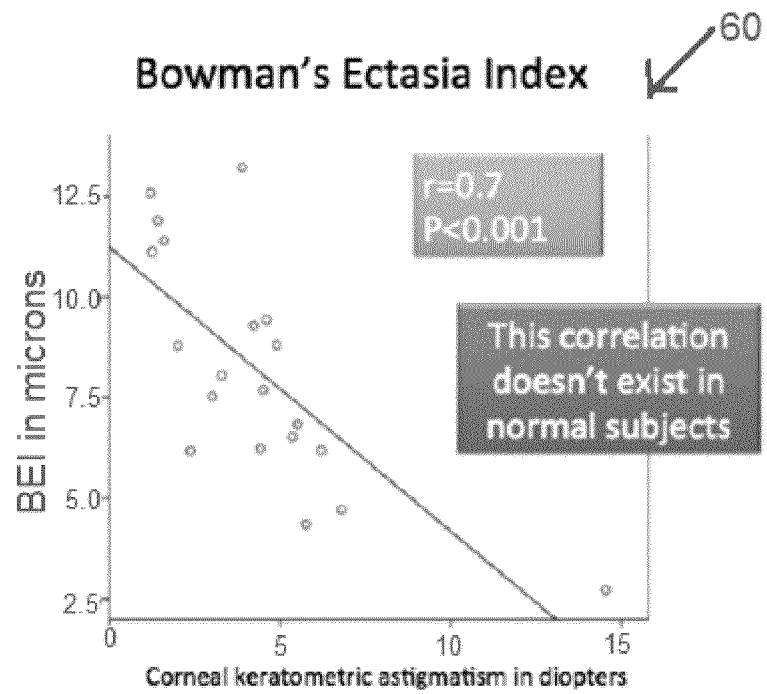
FIG. 8D shows a graph demonstrating the correlation between Bowman's Ectasia Index and corneal keratometric astigmatism.
Figure 8E:
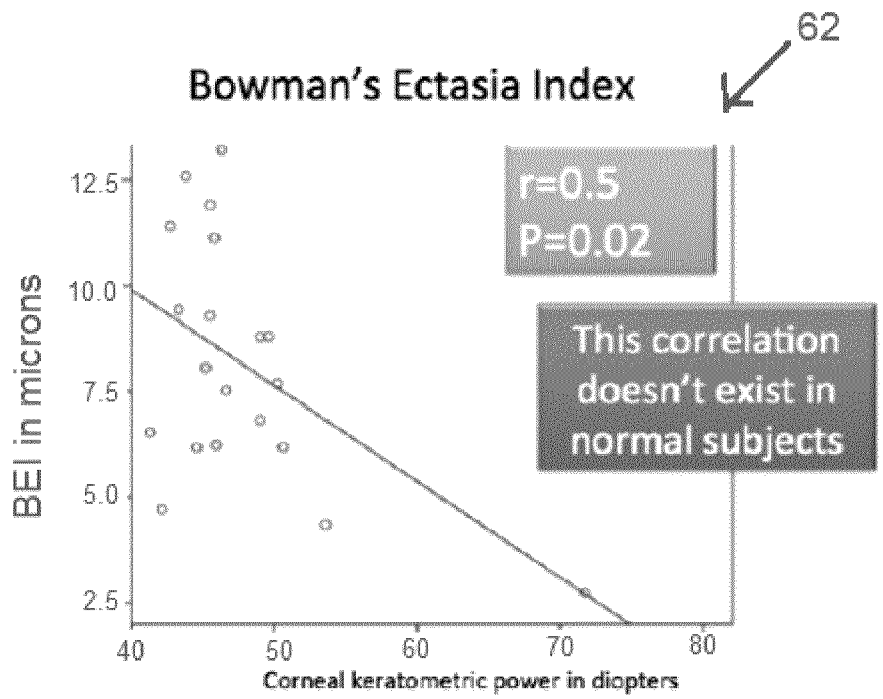
FIG. 8E shows a graph demonstrating the correlation between Bowman's Ectasia Index and keratometric power.
Figure 9:
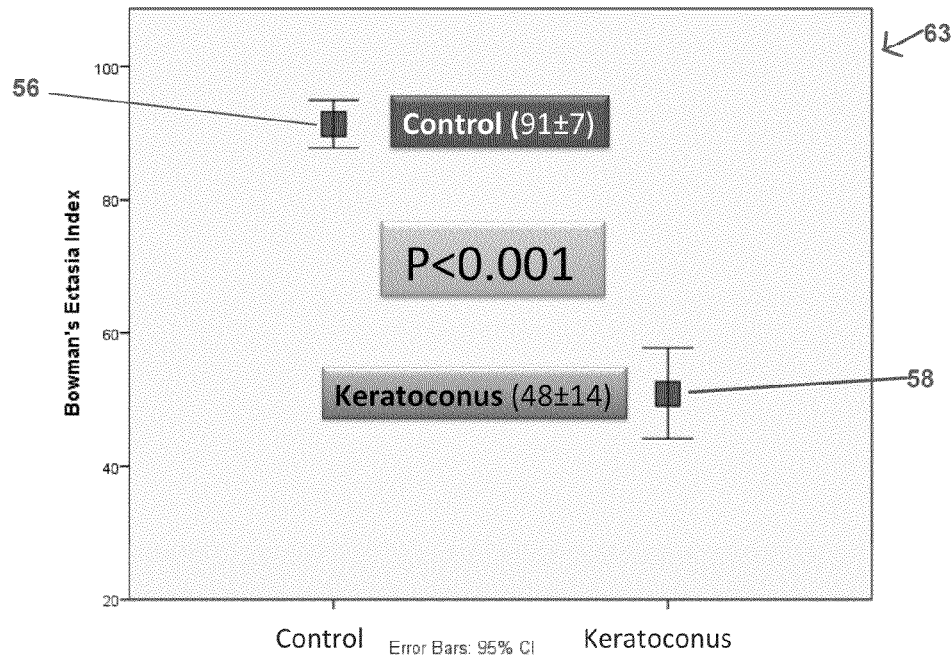
FIG. 9 shows a graph demonstrating the correlation between Enhanced Bowman's Ectasia Index and keratoconus.

Referring now to FIGS. 8A-8C, graphs comparing Bowman's layer thickness between control patients 56 and keratoconus patients 58 are shown. Characteristics of the control and keratoconus groups are shown in Table 2 below:

TABLE 2

| | Control Group | Keratoconus Group | P Value |
| --- | --- | --- | --- |
| Age | 33 ± 5 yrs | 37 ± 10 yrs | 0.19 |
| Gender | | | |
| Female | 8 | 8 | 1.00 |
| Male | 7 | 7 | 1.00 |
| Mean best spectacle-corrected logMAR VA | 0 (20/20) | 0.17 ± 0.12 (~20/30) | 0.001 |
| Thinnest corneal thickness | 526 µm ± 25 µm | 445 µm ± 36 µm | 0.001 |
| Avg-K | 43.2D ± 1.6D | 48.5D ± 7.3D | 0.011 |
| Ast-K | 0.8D ± 0.2D | 5.2D ± 3.0D | 0.001 |

In Table 2, "Ast-K" refers to astigmatic keratometry, "Avg-K" refers to average keratometry, "D" refers to diopters, "logMAR" refers to the logarithm of the minimum angle of resolution, and "VA" refers to visual acuity. One randomly selected eye per patient was included in the analysis. Values are presented as means±standard deviation.

The Bowman's layer can be mapped using custom-made software. For example, maps of 42 subjects, 20 controls and 22 ectasia patients (keratoconus) were created. BEI is defined as the thinnest point on the Bowman's layer measured on the 2D corneal map. Keratoconus patients have shown high statistical difference from the controls highlighting the utility of the index in diagnosis of the disease. BRT is defined as the difference between the thickest superior and thinnest inferior point on the Bowman's membrane map. As shown in FIG. 8C, the thinnest point on the Bowman's layer in normal patients 56 may be approximately 13 µm±2 µm, which is thicker than the thinnest point on the Bowman's layer in patients having keratoconus 58 (7 µm±3 µm). BRT shows similar results to BEI and serves as another index that can confidently differentiate controls from keratoconic patients in a highly statistically significant manner. In the graphs 60, 62 in FIGS. 8D and 8E, the correlations between Bowman's Ectasia Index (BEI) and keratometric astigmatism and keratometric power, respectively, are shown. BEI correlates accurately with disease severity: the more severe the ectasia, the lower the associated BEI value. Correlations with keratometric astigmatism and keratometric power of the cornea in the ectasia group highlight that property. BEI may be approximately 90% or more sensitive and approximately 90% or more specific for the diagnosis of ectasia.

An additional index, the enhanced BEI (eBEI), may be used to describe the relative thinning rather than absolute thinning of the inferior Bowman's layer. That is, the index compares the inferior thinnest point of the Bowman's layer to the patient's own normal Bowman's layer thickness. For example, eBEI may be calculated by dividing the Bowman's layer minimum inferior thickness by the average thickness of the superior Bowman's layer and then multiplying the result by 100:

$$\frac{\text{Bowman's layer minimum inferior thickness}}{\text{Bowman's layer superior average thickness}} \times 100$$

Another index may also be used, referred to as eBEI-Max, which may be calculated by dividing the Bowman's layer minimum inferior thickness by the maximum thickness of the superior half of the cornea and then multiplying the result by 100:

$$\frac{\text{Bowman's layer minimum inferior thickness}}{\text{Bowman's layer superior average thickness}} \times 100$$

eBEI and eBEI-Max both showed highly significant difference in keratoconus compared to normal subjects (48±1 vs. 91±7; P<0.001 for eBEI, 40±13 vs. 75±8 for eBEI-Max). Receiver-operating characteristics (ROC) curve analysis showed excellent predictive accuracy for eBEI and eBEI-Max in the diagnosis of keratoconus with 100% sensitivity and specificity (area under the curve, or AUC, being 1) in a pilot study with a cut-off values of 80 and 60, respectively. AUC of inferior Bowman's layer average thickness and minimum thicknesses were 087 and 0.96 with a sensitivity of 80% and 93, respectively, and specificity of both was 93%. Inferior Bowman's layer average thickness, inferior Bowman's layer minimum thickness, eBEI, and eBEI-Max correlated highly to keratometric astigmatism (Ast-K) (R=−0.72, −0.82, −0.84, and −0.82, respectively; P<0.001) and to average keratometric readings (Avg-K) (R=−0.62; P<0.001, R=−0.59; P=0.001, R=−0.60; P<0.001, and R=−0.59, P=0.001, respectively). Thus, Bowman's layer vertical topographic thickness maps of keratoconus patients disclose characteristic localized relative inferior thinning. Inferior Bowman's layer average thickness, inferior Bowman's layer minimum thickness, eBEI, and eBEI-Max are qualitative and quantitative indices for the diagnosis of keratoconus that accurately correlate with the severity of keratoconus (as shown in the graph 63 of FIG. 9). The characteristics of the Bowman's layer indices calculated on topographic thickness maps of the layer in normal subjects and patients with keratoconus are shown in Table 3 below:

ectasia index (defined as Bowman's layer minimum thickness of the inferior half of the cornea divided by Bowman's layer average thickness of the superior half of the cornea multiplied by 100), "eBEI-Max" refers to enhanced Bowman's ectasia index (defined as Bowman's layer minimum thickness of the inferior half of the cornea divided by Bowman's layer maximum thickness of the superior half of the cornea multiplied by 100), "BL" refers to Bowman's layer, and "KC" refers to keratoconus. The sensitivity, specificity, and cutoff values were chosen to maximize total diagnostic accuracy (to minimize the total number of errors).

Descemet's Membrane Thickening Index (DMT), Descemet's Rejection Index (DRI), and Descemet's Membrane Irregularity Factor (DIF)

Referring generally to FIGS. 10A-13B, figures relating to Descemet's Membrane Thickening Index (DMT), Descemet's Rejection Index (DRI) and Descemet's Membrane Irregularity Factor (DIF) are shown. In another aspect of the present invention is based on the concept that on creating a 2D map of the Descemet's membrane (DM), indices can be calculated that is diagnostic for diseases such as keratoplasty rejection and failure and Fuchs' dystrophy. These indices are referred to as DMT, DRI, and DIF. DMT is calculated as the average thickening of DM calculated on 2D or 3D maps of the membrane, while DIF is calculated as the standard deviation of the DM thickness along 2D or 3D maps of the cornea. In cases with active keratoplasty rejection, severe thickening of the DM can be seen on 2D or 3D maps of the membrane, which translates to a high DMT. DMT of failed keratoplasty shows a highly statistically significant thickening compared to normal eyes and functional grafts (p<0.001).

Response to treatment leads to a decrease of DMT, but not back to a baseline level. So, each rejection episode leaves a "fingerprint" on the DM in the form of permanently elevated DMT. Thus, DMT is an index that describes the presence of current rejection episode by detecting severe thickening, response to treatment of the current episode by detecting a decrease in DMT and, more importantly, the insult that has occurred on the graft from previous rejection episodes by comparing DMT to controls. Thus, DMT serves as a diagnostic factor of rejection and failure and a prognostic factor of the survival of keratoplasty graft. This can signal to the treating

TABLE 3

| | Control (μm) | KC (μm) | P Value | AUC | Sensitivity | Specificity | Cutoff (μm) | Correlation to Avg-K Readings | Correlation to Ast-K |
|---|---|---|---|---|---|---|---|---|---|
| BL total average thickness | 15 ± 1 | 13 ± 2 | 0.056 | 0.78 | 60% | 93% | 13.3 | R = −0.48, P = 0.007 | R = −0.53, P = 0.002 |
| BL average thickness of the inferior half of the cornea | 15 ± 2 | 12 ± 3 | <0.001 | 0.87 | 80% | 93% | 13.5 | R = −0.62, P < 0.001 | R = −0.72, P < 0.001 |
| BL minimum thickness of the inferior half of the cornea | 13 ± 2 | 7 ± 3 | <0.001 | 0.96 | 93% | 93% | 11.5 | R = −0.59, P = 0.001 | R = −0.82, P < 0.001 |
| BEI (no units) | 91 ± 7 | 48 ± 14 | <0.001 | 1.00 | 100 | 100 | 80 | R = −0.60, P < 0.001 | R = −0.84, P < 0.001 |
| BEI-Max (no units) | 75 ± 8 | 40 ± 13 | <0.001 | 1.00 | 100 | 100 | 60 | R = −0.59, P = 0.001 | R = −0.82, P < 0.001 |

In Table 3, "Ast-K" refers to keratometric astigmatism, "AUC" refers to area under the curve, "Avg-K" refers to average keratometric, "eBEI" refers to enhanced Bowman's physician a need to salvage a potentially failing and/or rejecting graft and possibly more aggressive treatment and monitoring.

In Fuchs' dystrophy, calculating DMT and DIF from the DM 2D or 3D maps can allow for diagnosis and monitoring of the disease and can diagnose sub-clinical disease in donor corneal graft in the eye bank. As the disease advances, measured DMT will increase. Advanced disease will exhibit more guttae, which can be quantified by DIF. This quantification describes the irregularity of the DM and, thus, the load of guttae, which corresponds to the stage of the disease. As such, DMT and DIF are qualitative and quantitative diagnostic criteria for the diagnosis of Fuchs' dystrophy that can aid in diagnosing and monitoring the disease in the clinic as well as in eye banks.

Further, it has been found that thickening of the DM occurs in cases of Fuchs' dystrophy and keratoplasty rejection and failure. Detecting a thickening of the allograft basement membranes may be indicative of graft rejection. Normally, the Descemet's membrane (DM) thickens by 1.3 µm±0.2 µm per decade (every ten years). For example, the average DM thickness for a young person is 10 µm±3 µm and the average DM thickness for an elderly person is 16 µm±2 µm. Currently known methods are not able to create a map of the membrane to calculate the thickening, such as by averaging a reflectivity profile created from the OCT image using at least two spikes on the reflectivity profile as the edges of the DM. Further, such methods do not provide sufficient accuracy, as lesions attached to the DM as keratic precipitates and guttae are often inadvertently incorporated into the measured thicknesses. The present invention has overcome these problems, and provides a means for creating 2D or 3D maps of the DM usable to measure the thickness of the membrane accurately enough to calculate the factor DMT.

Figure 10A:
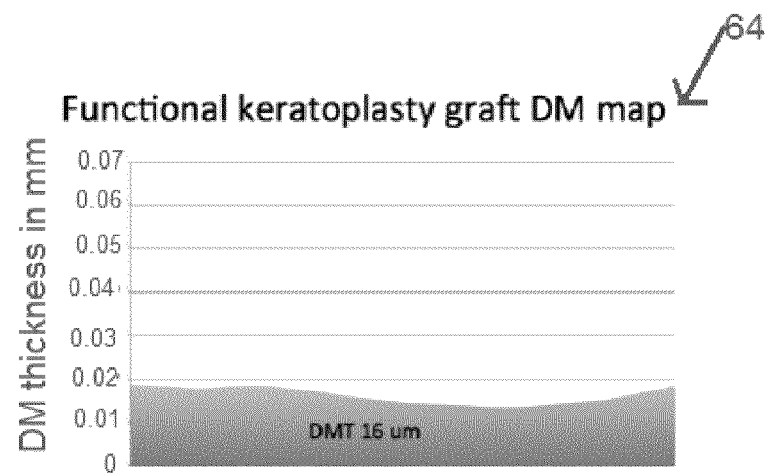
FIGS. 10A-10C show graphs demonstrating a correlation between Descemet's Membrane Thickening Index and outcome of keratoplasty.
Figure 10B:
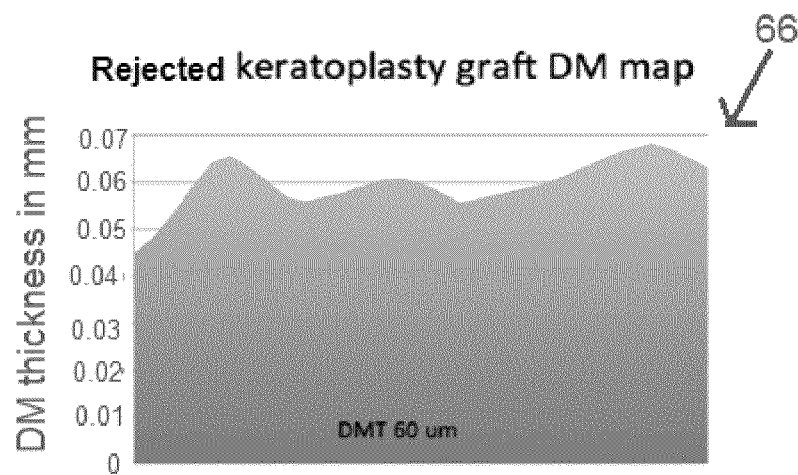
Figure 10C:
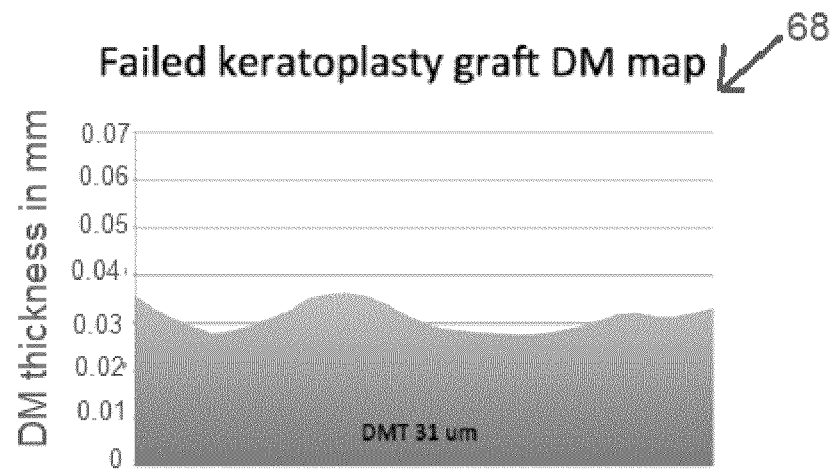

Referring now to FIGS. 10A-10C, graphs 64, 66, 68 demonstrating a correlation between Descemet's Membrane Thickening Index (DMT) and outcome of keratoplasty are shown. As is shown in FIGS. 10A-10C, DMT is thicker in a rejecting penetrating keratoplasty graft (FIG. 10B) and a failed penetrating keratoplasty graft (FIG. 11C) than in a functional penetrating keratoplasty graft (FIG. 10A) (P<0.001), and DMT is thicker in a rejecting keratoplasty graft (FIG. 10B) than in a failed keratoplasty graft (FIG. 10C).

Figure 11A:
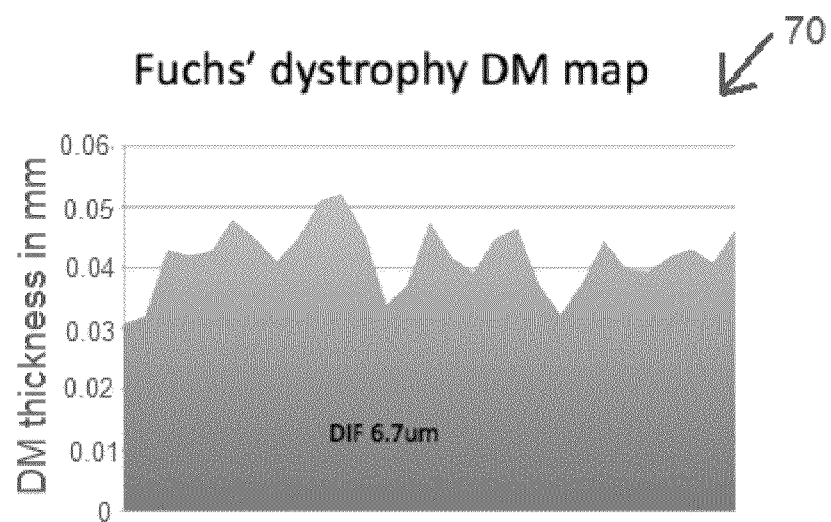
FIGS. 11A and 11B show graphs demonstrating a comparison between Descemet's Membrane Irregularity Factor in normal patients and Fuchs' dystrophy patients.
Figure 11B:
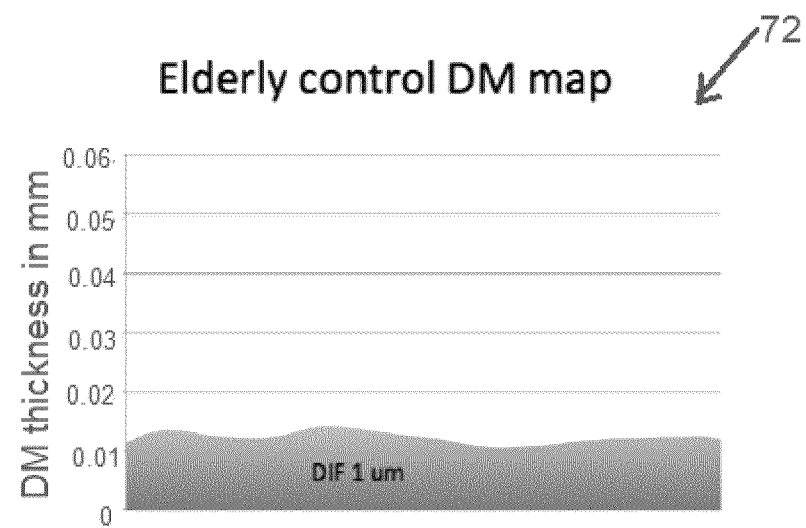

Referring now to FIGS. 11A and 11B, graphs 70, 72 demonstrating a comparison between Descemet's membrane irregularity factor in normal patients and Fuchs' dystrophy patients is shown. DMT and DIF are significantly elevated in Fuchs' dystrophy patients (FIG. 11A) compared to elderly control patients (FIG. 11B).

In addition to DMT, a supplemental index called Descemet's Rejection Index (DRI) may be used, which isolates the intrinsic thickening of the DM from the generalized thickening of a swollen cornea. DRI may be calculated using the following equation:

$$\frac{\text{Descemet's membrane thickness}}{\text{Total corneal thickness}} \times \text{Constant}$$

The value of the constant may be 33, determined because when using this constant the mean DRI of an age-matched control group in a pilot study equaled 1.

In corneal graft rejection, Descemet's membrane undergoes thickening that can be detected and quantified. Use of DMT with DRI may allow for the detection of acute and chronic graft rejection and immunological failure. Data showed that patients with functional grafts having a history of previous rejection episodes had abnormal DMT and DRI. This suggests that immunological insults to the graft leave a fingerprint on its DM that can be traced and quantified using DMT and DRI. Moreover, in cases with acute rejection, DM structural changes were significant when only minimal clinical signs were noted, suggesting that they can be used to detect subclinical rejection episodes. Thus, using DMT and DRI may allow for the diagnosis of active graft rejection and may differentiate between rejection and failure secondary to non-immunological causes.

Figure 12A:
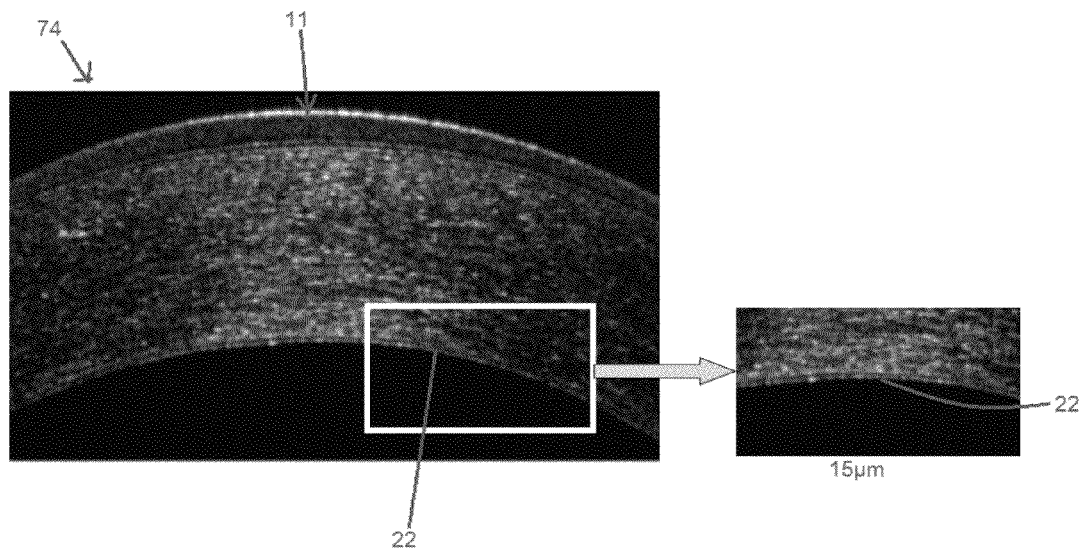
FIG. 12A shows an OCT image and a magnified insert of the Descemet's membrane of a functional keratoplasty.
Figure 12B:
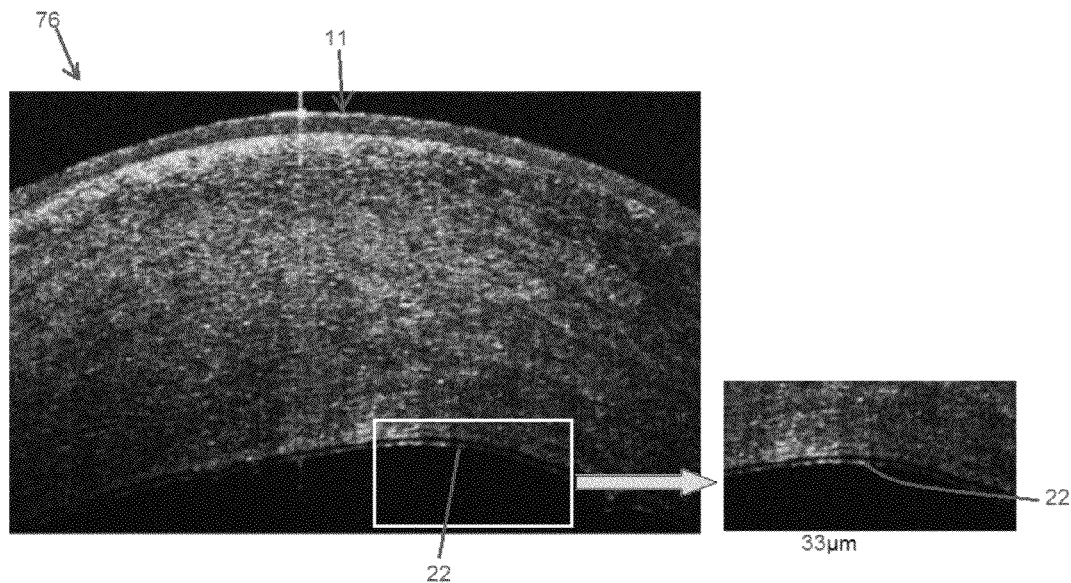
FIG. 12B shows an OCT image and a magnified insert of the Descemet's membrane of a rejected keratoplasty.

In one study, 71 eyes were examined. Of these, 27 had functional grafts, nine were actively rejecting grafts, nine had already rejected grafts, seven had failed grafts secondary to non-immunological causes, and 19 were age-matched control eyes. DMT and DRI of functional corneal grafts (as shown in FIG. 12A) showed no statistically significant difference from those of the control group (17 µm vs. 16 µm and 1.1 vs. 1; P>0.05). FIG. 12A shows an OCT image 74 of the cornea 11, including the Descemet's membrane, and a close-up view of the Descemet's membrane 22, which has a thickness of approximately 15 µm. On the other hand, actively rejecting grafts showed a significantly higher DMT and DRI than those of functional grafts (29 µm vs. 17 µm and 1.7 vs. 1.1, respectively; P<0.001). In rejected grafts (as shown in FIG. 12B), DMT and DRI were significantly higher than those of the actively rejecting grafts (P=0.01 and P=0.02, respectively). FIG. 12B shows an OCT image 76 of the cornea 11, including the Descemet's membrane, and a close-up view of the Descemet's membrane 22, the Descemet's membrane displaying visible thickening to approximately 33 µm. Thus, DMT and DRI may be used to differentiate between functional grafts, grafts that are being actively rejected, and grafts that have already been rejected.

To evaluate whether DMT and DRI are specific to the immunological rejection and if damage to the graft secondary to immunological insult can be differentiated from damage due to a non-immunological insult, the indices obtained from rejected grafts and indices obtained from failed grafts secondary to non-immunological causes were compared. While no statistically significant difference existed between corneal thicknesses (CCT) of the two groups, DMT and DRI of rejected grafts were significantly higher than in the non-immunologically failed grafts (53 µm vs. 24 µm and 1.95 vs. 1.04; P<0.001). Actively rejecting grafts showed significantly higher DRI compared to control grafts (1.41 vs. 1.15; p=0.001), when CCT showed only a non-significant increase (607 µm vs. 553 µm; p=−0.15). On correlating the DMT to CCT in the study groups, it was found that no significant correlations existed in the normal eyes, whereas in the rejected group that correlation was highly significant (r=0.9; P<0.001), indicating that DM thickening is an excellent descriptor of the severity of rejection. In the functional grafts group, significant correlation was noted (r=0.5; P<0.1), suggesting that DM thickening might be an indicator of subclinical graft dysfunction in those patients. Grafts that failed to respond to treatment (n=6) showed further increase in DRI (1.43 to 1.77; P<0.05). In grafts where rejection was reversed (n=3), DRI stabilized. In control grafts, DRI was stable throughout follow up. In another study, functional grafts with history of rejection episodes were found to have thicker DM than those with no history of rejection episodes. Both groups were clear and undistinguishable by clinical examination. This thickening is suggestive that past rejection insults leave "fingerprints" in the form of residual thickening on the DM that can be detected and quantified. Thus, DRI and DMT may be useful in diagnosing active corneal graft rejection. Failure of treatment may lead to further significant increase in DRI whereas successful rejection reversal may stabilize DRI. In another study, CCT failed to differentiate between rejected grafts and failed grafts secondary to non-immunological causes, while DRI was 100% sensitive and specific in differentiating between the two groups (AUC of 1; P<0.001).

Furthermore, it was shown that actively rejecting grafts showed significantly higher CCT, DMT, and DRI compared to control grafts (570 μm vs. 520 μm; P=0.031, 27 μm vs. 17 μm; P=0.0001, 1.54 vs. 1.1; P=0.0001, respectively). Receiver operating characteristic curve analysis showed very high predictive accuracy of DMT and DRI (area under the curve (AUC) of 0.97 and 0.96, respectively) that was significantly higher (P<0.001) than in CCT (AUC 0.65). DMT was 100% sensitive and 89% specific (optimal cutoff value of 20 μm) and DRI was 100% sensitive and 74% specific (optimal cutoff value of 1.17), while CCT was only 73% sensitive and 59% specific (optimal cutoff value of 550 μm). Thus, DMT and DRI have high predictive accuracy, sensitivity, and specificity in diagnosing active corneal graft rejection that is significantly better than the predictive accuracy, sensitivity, and specificity of CCT.

The anterior segment OCT indices described herein can be incorporated into current or future OCT machines (such as UHR-OCT), or any other imaging device that can provide high-resolution images of the cornea and ocular surface, and used in everyday clinics. Enhanced epithelial irregularity factor (eEIF) can aid in the diagnosis, management, and monitoring of dry eye syndrome (DES) and can detect the response to treatment, thus also being usable in the testing of new therapies. Enhanced EIF can detect patients who are symptomatic secondarily due to microscopic injury of their ocular surface brought about by DES and missed by the other diagnostic techniques that are not accurate enough to detect such signs. Further, eEIF can be used to monitor patient response to treatment, as it is standardized and quantitative. Still further, eEIF can be used in research because it is useful in testing the effectiveness of new therapies in an objective accurate method. Bowman's Ectasia Index (BEI), enhanced Bowman's Ectasia Index (eBEI and eBEI-Max), and Bowman's Relative Thinning Index (BRT) can be incorporated into future OCT and aid in the diagnosis of early cases of ectasia, thus allowing for early intervention to prevent further progression as well as prescreening refractive surgery candidates. Likewise, Descemet's Membrane Thickening Index (DMT), Descemet's Rejection Index (DRI) and Descemet's Membrane Irregularity Factor (DIF) can be incorporated into future OCT systems and be used to detect keratoplasty graft rejection and failure, response to treatment, and, more importantly, the insult that has occurred on the graft from previous rejection episodes. These indices serve as diagnostic factors for rejection and prognostic factors for the survival of the graft. This can signal to the treating physician a need to salvage a potentially failing and/or rejecting graft and possibly more aggressive treatment, follow up, and prophylactic treatment. DMT and DIF can also be used as qualitative and quantitative diagnostic criteria for the diagnosis of Fuchs' dystrophy that can aid in diagnosis and monitoring of the disease in the clinic and in studying donor corneal grafts in the eye bank.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of evaluating dry eye syndrome in a patient, the method comprising:
   obtaining high-resolution images of the patient's cornea using an imaging system, the cornea including an epithelium, the images being taken in at least four frames that divide the cornea into at least eight segments;
   calculating an enhanced epithelial irregularity factor (eEIF) value for each of the at least eight segments, the eEIF value being the mean of the standard deviation of epithelial thickness measured along each of the at least four frames;
   calculating an average eEIF value, the average eEIF value being the average of the at least eight eEIF values; and
   comparing the average eEIF value to a predetermined eEIF value.

2. The method of claim 1, wherein the imaging system is an optical coherence system.

3. The method of claim 2, wherein the at least four frames includes four frames that are at approximately 45 degrees, approximately 90 degrees, approximately 135 degrees, and approximately 180 degrees.

4. The method of claim 3, wherein the epithelial thickness is measured over the central 3 mm of the cornea of each frame.

5. The method of claim 4, wherein the method further comprises converting the optical coherence images with a computer processor to a reflectivity profile that represents one or more corneal layers.

6. The method of claim 1, wherein dry eye syndrome is considered to be present when the average eEIF value is higher than the predetermined eEIF value.

7. The method of claim 1, further comprising evaluating the efficacy of a treatment for dry eye syndrome based at least in part on the comparison between the average eEIF value to a predetermined eEIF value, wherein the treatment is considered to be effective when the average eEIF value and the predetermined eEIF value are within a predetermined range of each other.

8. The method of claim 1, wherein the optical coherence system is an ultrahigh-resolution optical coherence system and includes a telecentric probe coupled to a slit lamp, the ultrahigh-resolution optical coherence system obtaining 24 frames per second.

* * * * *